(12) United States Patent
Ehninger

(10) Patent No.: US 11,944,375 B2
(45) Date of Patent: Apr. 2, 2024

(54) ELECTROSURGICAL RETURN ELECTRODES HAVING FABRIC CONDUCTIVE ELEMENTS

(71) Applicant: Megadyne Medical Products, Inc., Draper, UT (US)

(72) Inventor: Michael D. Ehninger, South Jordan, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 353 days.

(21) Appl. No.: 17/004,755

(22) Filed: Aug. 27, 2020

(65) Prior Publication Data

US 2021/0085392 A1 Mar. 25, 2021

Related U.S. Application Data

(60) Provisional application No. 62/904,465, filed on Sep. 23, 2019.

(51) Int. Cl.
| | | |
|---|---|---|
| A61B 18/16 | (2006.01) | |
| A61B 17/00 | (2006.01) | |
| A61B 18/00 | (2006.01) | |

(52) U.S. Cl.
CPC .... *A61B 18/16* (2013.01); *A61B 2017/00902* (2013.01); *A61B 2017/00929* (2013.01); *A61B 2018/00077* (2013.01); *A61B 2018/00083* (2013.01); *A61B 2018/167* (2013.01)

(58) Field of Classification Search
CPC ............... A61B 18/1233; A61B 18/16; A61B 2018/00077; A61B 2018/00083; A61B 2018/00595; A61B 2018/00601; A61B 2018/0063; A61B 2018/1253; A61B 2018/167; A61B 2017/00902; A61B 2017/00929
See application file for complete search history.

(56) References Cited

U.S. PATENT DOCUMENTS

| | | | | |
|---|---|---|---|---|
| 4,088,133 | A | * | 5/1978 | Twentier ................ A61B 18/16 606/32 |
| 8,876,812 | B2 | | 11/2014 | Aramayo |
| 2001/0029367 | A1 | * | 10/2001 | Fleenor .................. A61B 50/13 607/152 |
| 2013/0237983 | A1 | | 9/2013 | Giles et al. |
| 2015/0373781 | A1 | * | 12/2015 | Augustine ............. H05B 3/145 219/217 |
| 2017/0360505 | A1 | | 12/2017 | Ehninger et al. |

FOREIGN PATENT DOCUMENTS

WO 2016/077742 5/2016

* cited by examiner

*Primary Examiner* — Khadijeh A Vahdat
(74) *Attorney, Agent, or Firm* — Workman Nydegger

(57) ABSTRACT

An electrosurgical system comprises a return electrode that includes a conductive element disposed between two pads. The conductive element comprises a flexible, conductive fabric material and an electrical bus bar disposed along an edge of the fabric. The return electrode, including the conductive element, is transparent to RF waves and other wavelengths used in medical imaging systems.

17 Claims, 14 Drawing Sheets

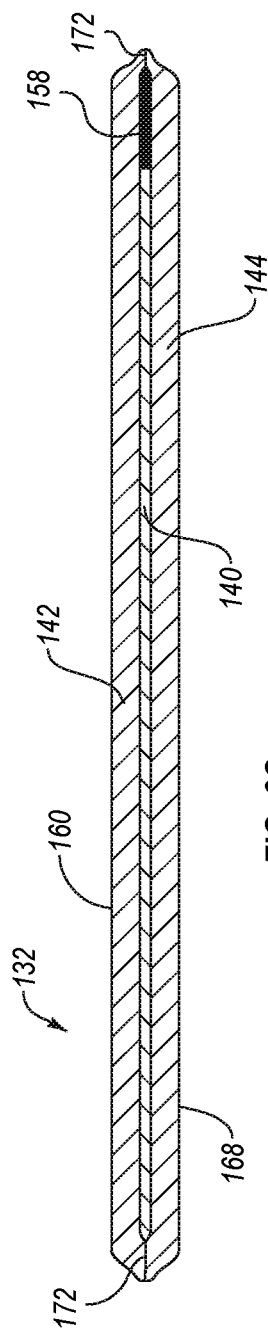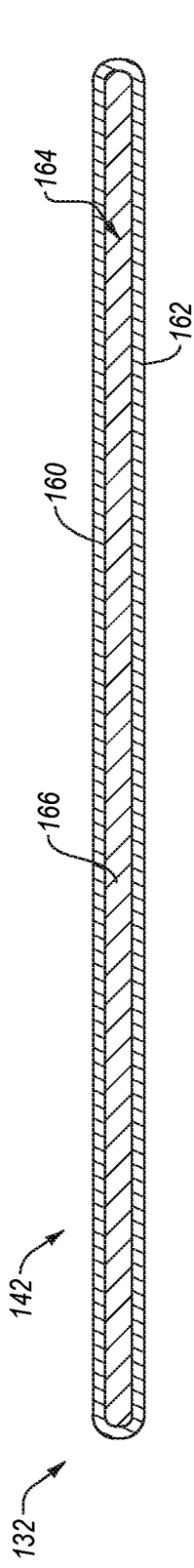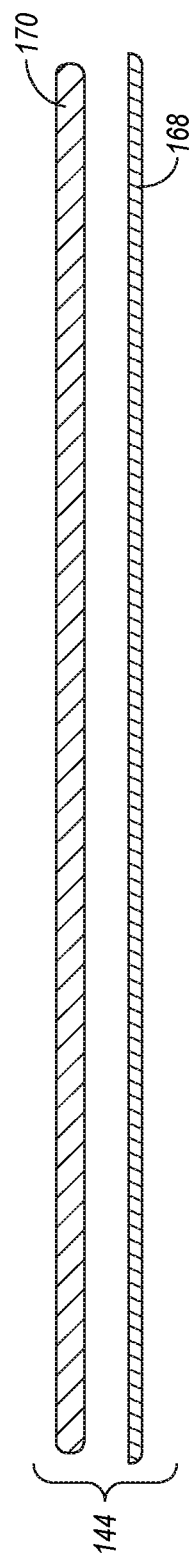

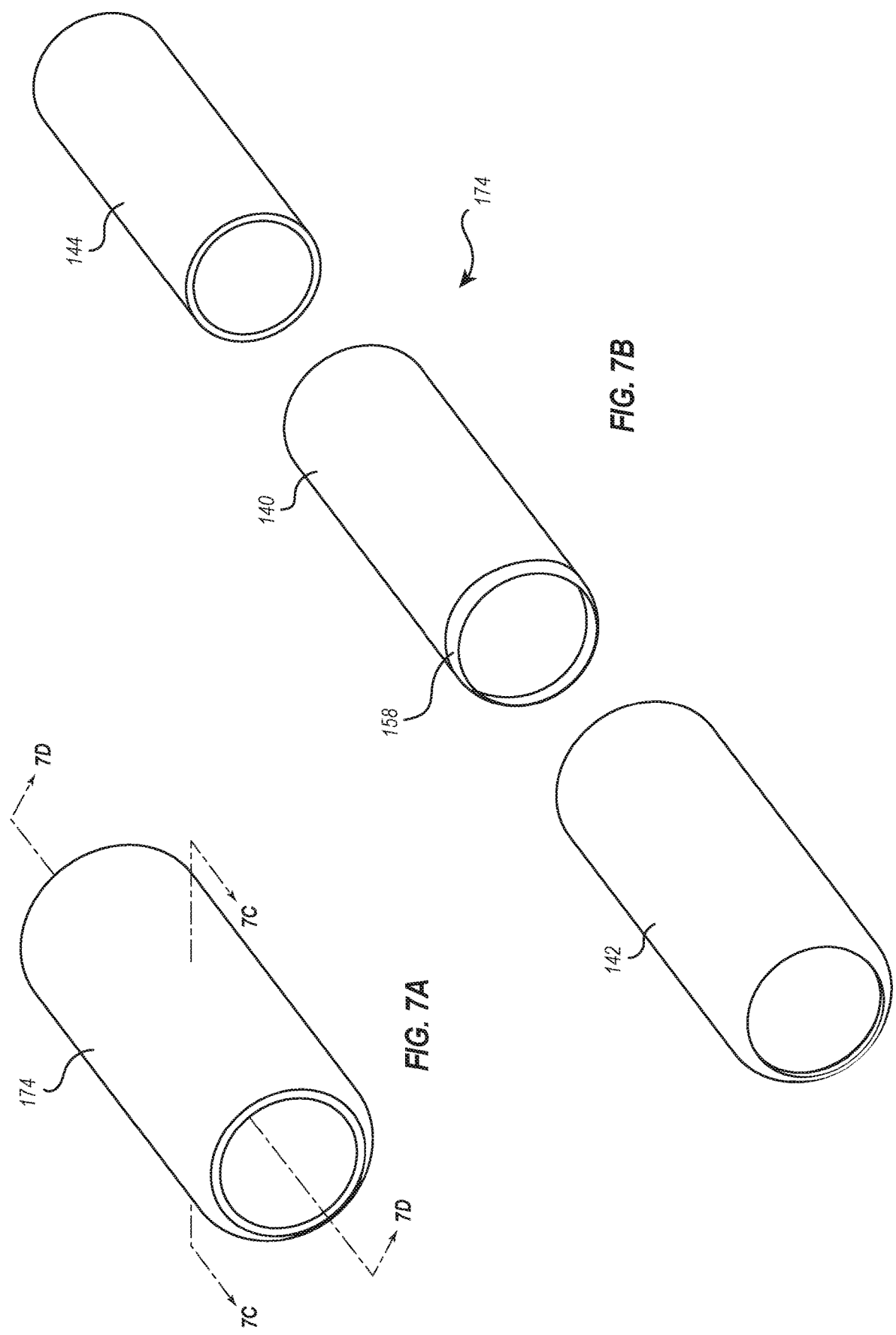

ELECTROSURGICAL RETURN ELECTRODES HAVING FABRIC CONDUCTIVE ELEMENTS

CROSS-REFERENCE TO RELATED APPLICATIONS

This application claims priority to and the benefit of U.S. Patent Application No. 62/904,465, filed Sep. 23, 2019, and entitled Electrosurgical Return Electrode Having Fabric Conductive Elements, the entire content of which is incorporated herein by reference.

BACKGROUND

1. Technical Field

The present disclosure relates generally to electrosurgical systems. In particular, the present disclosure relates to return electrodes.

2. The Relevant Technology

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by an RF energy source, such as a wave generator or Electro-Surgical Unit (ESU), and transmitted to a patient's tissue through a hand-held electrode that is operated by a surgeon.

Monopolar electrosurgical generator systems have an active electrode that is applied by the surgeon to the patient at the surgical site to perform surgery and a return path from the patient back to the ESU. The active electrode at the point of contact with the patient must be small in size to produce a high current density in order to produce a surgical effect of cutting or coagulating tissue. The return electrode, which carries the same current as the active electrode, has a large enough effective surface area in contact with the patient such that a low density current flows from the patient to the return electrode. An electrical return cable connected to the return electrode provides a conventional electrical return to the electrosurgical radio frequency energy source.

Since the inception of electrosurgery, various types of return electrodes have been used, including self-limiting return electrodes. Unlike typical sticky pads and steel plate return electrodes, self-limiting return electrodes are relatively large, thereby eliminating the need for conductive gels that may irritate a patient's skin. Additionally, self-limiting return electrodes typically employ geometries and materials whose impedance characteristics, at typically used electrosurgical frequencies, are such that the return electrode self-limits current densities (and corresponding temperature rises) to safe thresholds, should the contact area between the patient and the electrode be reduced below otherwise desirable levels. Furthermore, self-limiting return electrodes were specifically designed to evenly distribute the current density over the entire contact area between the patient and the return electrode in order to reduce the risk of patient burns.

Typical self-limiting return electrodes are commonly made in multiple sizes for different sized patients. For instance, a typical self-limiting return electrode for a relatively small person (e.g., under 50 lbs.) may be about 26×12 inches while a typical self-limiting return electrode for a larger person may be about 46×20 inches.

As noted above, an electrical return cable connected to the return electrode provides an electrical return to the electrosurgical radio frequency energy source. The more consistent and secure the contact between the patient and the return electrode, the more effective the return electrode will be in safely drawing current from the patient and returning the current to the power source or shared ground thereof.

Some return electrodes consist of a flat, laminar structure disposed on top of an operating table, which could result in inconsistent contact between the patient and the return electrode during use. For example, due to the contours of the human body, some areas of the body may not contact return electrodes when laid upon. In addition, any movement or repositioning of the patient during use may cause variations in the contact area between the patient and the return electrode.

Also, as noted above, dimensions of some existing return electrodes vary to accommodate patients of different sizes. Small return electrodes may not be large enough to form suitable contact with the patient and larger return electrodes may be unnecessarily big and inconvenient for smaller patients on smaller operating tables or beds.

Furthermore, return electrodes consisting of laminar pads may limit available areas of a patient's body with which the return electrode can make contact. For example, laminar pad return electrodes may be limited to only contact the back side of a patient lying on his or her back or only the front side of a patient lying on his or her front side. However, a surgeon or other medical professional may desire the return electrode to contact the patient at certain, specific locations of the body depending on the type of operation being performed and the part of the body being operated upon.

In addition, typical return electrodes include a conductive element that includes a conductive material suitable for carrying electrical current from the patient to the return cable, as noted above. Usually, the same conductive materials used for the conductive element in the return electrode are not transparent for use with certain medical imaging techniques. For example, surgical instruments, such as scalpels, sponges, clamps, and other instruments may have RFID tags that medical personnel can identify during and post-surgery using an antenna positioned underneath the patient. This may be done to ensure that no instruments are misplaced within the patient prior to the closing of surgical wounds. However, typical return electrodes may not be transparent to radio frequency signals and would thus obscure the identification of such instruments having RFID tags. Return electrodes may also obscure other imaging techniques used during surgeries, such as X-ray imaging and CT scanning.

As such, there are a number of problems in the art of return electrodes used in electrosurgical systems that can be addressed.

BRIEF SUMMARY

The present disclosure addresses the foregoing shortcomings by providing return electrodes having fabric conductive elements that are transparent to RF waves and other wavelengths used for medical imaging systems. For example, in one embodiment of the present disclosure, an electrosurgical return electrode includes a first pad, a second pad, and a conductive fabric layer disposed between the first and second pads.

In one embodiment, an electrosurgical return electrode includes a first pad, a second pad, and a conductive element disposed between the first and second pads. The conductive element includes a flexible fabric that is transparent to RF waves and a bus bar disposed along the edge of the flexible fabric.

In one embodiment, an electrosurgical system includes a return electrode. The return electrode includes a first pad, a second pad, and a conductive element disposed between the first and second pad. The conductive element is disposed between the first and second pads such that the first and second pads completely encompass the conductive element. The conductive element includes a flexible conductive fabric.

Additional features and advantages of the disclosed embodiments will be set forth in the description which follows, and in part will be obvious from the description, or may be learned by the practice of the disclosure. These and other features will become more fully apparent from the following description and appended claims or may be learned by the practice of the present disclosure.

BRIEF DESCRIPTION OF THE DRAWINGS

To further clarify the above and other advantages and features of the present disclosure, a more particular description will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 6C illustrates a cross-sectional view of the return electrode illustrated in FIG. 6A;

FIG. 6D illustrates an exploded view thereof;

FIG. 7A illustrates an embodiment of a return electrode, according to the present disclosure;

FIG. 7B illustrates an exploded view thereof;

DETAILED DESCRIPTION

The present disclosure relates generally to electrosurgical systems. In particular, the present disclosure relates to return electrodes. Embodiments of return electrodes described in the present disclosure are adaptable to various sized patients and can maintain consistent and secure contact with the patient during use. In addition, return electrodes described herein are transparent to medical imaging techniques used during operations.

Figure 1:
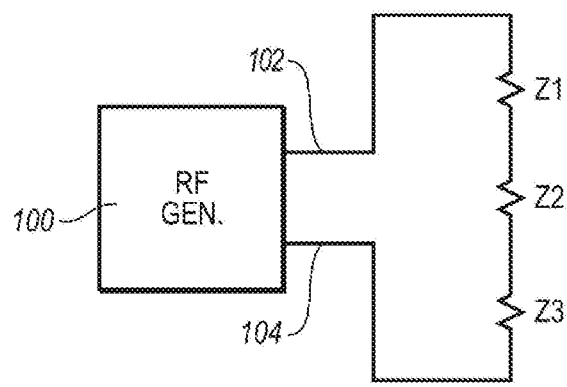
FIG. 1 illustrates an electrical schematic diagram of an embodiment of an electrosurgical system, according to the present disclosure.
Figure 2:
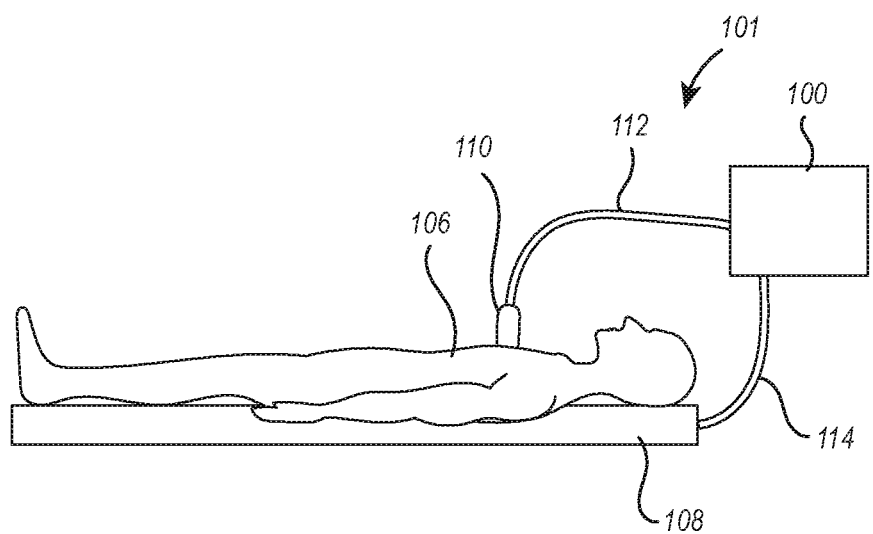
FIG. 2 illustrates an embodiment of an electrosurgical system, according to the present disclosure.
Figure 3:
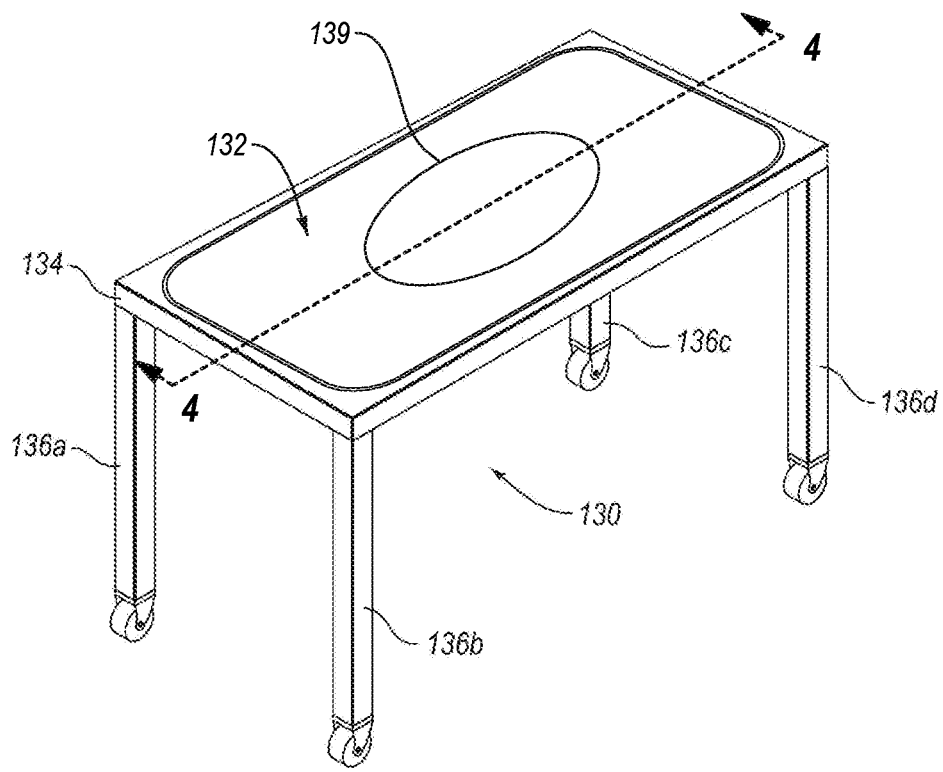
FIG. 3 illustrates an embodiment of a return electrode disposed on an operating table, according to the present disclosure.

FIGS. 1-4 and the corresponding discussion relate to the general structures and features of electrosurgical return electrodes that provide self-limiting characteristics and that can be used with patients of substantially any size. Turning to the drawings, and more particularly to FIGS. 1-3, a general discussion of self-limiting return electrodes and the general principles by which they operate will be provided. FIG. 1 thereof depicts a simplified electrical schematic diagram of an electrosurgical system illustrating typical impedances effectively included in the operative path of radio frequency current flow as presented to an electrosurgical generator during an operative procedure. There, it will be seen is conventional radio frequency electrical power generator 100, such as but not limited to constant power, voltage, and/or current or variable power, voltage and/or current generators.

Connected to electrical power generator 100 are conventional electrical conductors 102 and 104 which respectively connect generator 100 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 102 and 104 are representative of one illustrative structure that is capable of performing the function of connecting means for making electrical connection to the return electrode. It may be appreciated by one skilled in the art, however, that various other structures are appropriate and capable of performing the desired function.

Although the diagram of FIG. 1 is simplified and generally considers circuit elements in terms of the principal resistances, including the reactance contributed by the surgical instrument, the patient's body and the return electrode, so as to clearly and succinctly illustrate principles of the disclosure, it should be understood that in reality certain other parameters would be encountered, parameters such as distributed inductance and distributed capacitance which, for purposes of clarity in illustration of the principles hereof, are deemed relatively small and so not considered at this point in this description.

FIG. 2 illustrates a practical application of the electrical schematic diagram illustrated in FIG. 1 in the form of an electrosurgical system 101. In FIG. 2, a patient 106 lies on a return electrode 108 during an operation in which a hand-held surgical electrode 110 is in contact with the patient 106. The electrical power generator 100 powers the surgical electrode 110 via power cable 112. During use, current flows from the electrical power generator 100 to the surgical electrode 110 and into the patient 106. The electrical current flows through the patient 106, into the return electrode 108 and then back to the electrical power generator 100, or common ground thereof, via return cable 114.

With reference back to FIG. 1, power cable 112 of FIG. 2 is analogous to conductor 102 and return cable 114 is analogous to conductor 104. In addition, as noted above, surgical electrode 110 is represented by impedance $z_1$ of FIG. 1 and return electrode 108 is represented by impedance $z_3$. Patient 106 is represented by impedance $z_2$.

Figure 4:
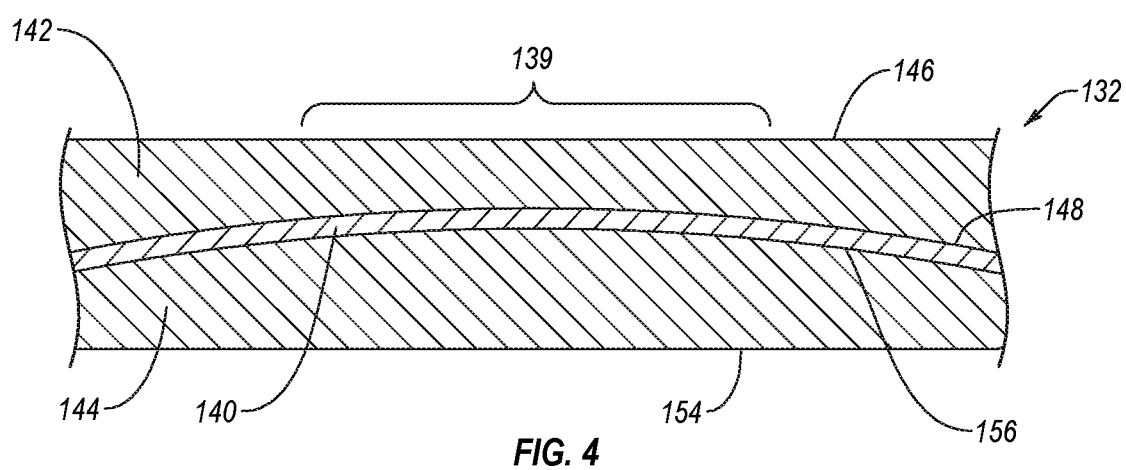
FIG. 4 illustrates a partial cross-sectional view of the return electrode illustrated in FIG. 3, according to the present disclosure.

Reference is now made to FIGS. 3-4, which illustrate an embodiment of an electrosurgical return electrode 132 according to the present disclosure. In FIG. 3, electrosurgical return electrode 132 is shown in perspective on operating table 130 with electrosurgical return electrode 132 according to the present disclosure disposed on the upper surface thereof, an edge of table 130 being identified by reference number 134. Operating table 130 is shown to have conventional legs 136a-136d that may be fitted with wheels or rollers as shown.

Table 130 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Although, in FIG. 3, the entire upper surface of table 130 is shown as being covered with return electrode 132, it should be understood that entire coverage is by no means required in order to practice the principles of the disclosure. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-third of the torso for an adult patient lying on an operating table or a portion of the buttocks of a patient sitting in a chair.

However, the effective working surface area will vary depending on the material used, in some geometrical configurations, and in instances where various layers of operating room linens are placed over the electrode. The principles hereof may be successfully employed, and the effective working surface area of the return electrode determined in such circumstances, by routine experimentation. Under certain conditions, the effective working surface may be as small as about seven square inches (or about 45 square centimeters).

The surface of return electrode 132 is preferably smooth and homogeneous and includes a thin resistive and/or dielectric layer. Alternatively, the surface of return electrode 132 may include a capacitive and/or inductive layer, depending on the particular operation of return electrode 132. The characteristics of the desired dielectric for the present embodiment are sufficiently comparable to those of selected rubbers, plastics and other related materials that the latter may be satisfactorily employed as materials for the return electrode.

As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

It will be observed that when return electrode 132 is laid out on operating table 130, the upper exposed, or working, surface of the electrode again is expansive so as to provide low impedance. Although it is not necessary that the electrode cover the entire surface of an operating table or the entire seat surface of a dental or other patient chair, it has been found advantageous in some instances to provide a greater surface area than that of the projected area of a portion of the buttocks or torso of a patient so that if a patient position shifts during the course of a procedure, a sufficient portion of the patient will remain in registration with the electrode surface so that the effective impedance will remain less than the above-described level.

Return electrode 132, as illustrated in FIGS. 3-4, may be made of conductive plastic, rubber, or other flexible material which, when employed in the electrode will result in an effective DC resistance presented by each square centimeter of working surface to be greater than about 8000Ω or alternatively provide a bulk impedance of greater than 4000 Ω·cm. Silicone, butyl rubber, or urethane have been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

FIG. 3 also illustrates that return electrode 132 includes an area 139. Area 139 of return electrode 132 may be adapted to have smaller patients positioned thereon. For instance, area 139 may be sized to have an infant sized patient positioned thereon. Furthermore, as discussed in greater detail below, return electrode 132, and particularly area 139 thereof, may be configured to provide the self-limiting characteristics discussed herein for infant sized patients positioned on area 139.

Although not illustrated, return electrodes may also include additional areas configured to provide self-limiting characteristics for patients from different industry standard weight categories. By way of non-limiting example, area 139 may be configured to provide self-limiting characteristics for patients under 5 kg, a second area may be configured to provide self-limiting characteristics for patients between 5 kg and 15 kg, and a third area may be configured to provide self-limiting characteristics for patients over 15 kg. In some embodiments the areas for different sized patients may overlap one another, while in other embodiments the areas do not overlap. Furthermore, the areas may be formed concentrically with one another.

Regardless of the specific arrangement of areas for different sized patients (e.g., non-overlapping, overlapping, concentric, etc.) return electrode 132 may include one or more visual indicators to identify the areas for different sized patients. For instance, area 139 may include a visual indicator that identifies area 139 as suitable for patients under 5 kg. Similarly, a second area may include a visual indicator that identifies the second area as suitable for patients between 5 kg and 15 kg, and a third area may include a visual indicator that identifies the third area as suitable for patients over 15 kg.

The one or more visual indicators may include labels, outlines, pictures, or other indicia that are printed or otherwise displayed on the outside surface(s) of return electrode 132. The one or more visual indicators may also or alternatively take the form of color coding. For example, each area of return electrode 132 may have a different color. The colors may be printed on return electrode 132 or the colors may be integrated into other components of return electrode 132. For instance, one or more components within area 139 may have a first color while one or more components in the other area(s) may have different colors so that the areas are distinguishable from one another.

Attention is now directed to FIG. 4, which illustrates a simplified, partial section taken along the lines 4-4 of FIG. 3. As illustrated in FIG. 4, return electrode 132 includes a conductive element 140 and pads 142, 144 on opposing sides of conductive element 140. Conductive element 140, in at least one embodiment, is made of a conductive woven fabric material. The woven fabric material of conductive element 140 is flexible and foldable. In at least one embodiment, the woven fabric material of conductive element 140 includes conductive fibers embedded into natural or synthetic woven fabric threads that are non-conductive. In at least one embodiment, the woven fabric material of conductive element 140 includes conductive fibers woven together into a fabric material.

When employed as a conductive element, such a conductive fabric material will result in an effective DC resistance presented by each square centimeter of the working surface of return electrode 132 (the surface that is in contact with or in close proximity to the patient) to be greater than about 8000 ohms or alternatively provide a bulk impedance of greater than 4000 Ω·cm.

Various conductive fibers may be woven or incorporated into a woven fabric material to give the required impedance. For example, conductive fibers such as carbon black, quantities of gold, silver, nickel, copper, steel, iron, stainless steel, brass, aluminum, or other conductors, or other conductive metal fibers have been found to be particularly attractive materials for conductive element 140 as they are flexible, as well as readily washable, disinfectable, and sterilizable.

As noted above, one or more conductive fibers may be woven together to form conductive element 140 or one or more conductive fibers may be embedded into or otherwise incorporated into other synthetic or natural woven threads to form conductive element 140. Such threads may include, but are not limited to, cotton, silk, wool, nylon, polyester, acrylic, or other fabrics known in the art.

In at least one embodiment, the woven fabric material of the conductive element 140 is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows conductive element 140 and return electrode 132, when the other components of return electrode 132 are transparent to one or more wavelengths of electromagnetic radiation, to be maintained in place during performance of certain medical procedures using particular wavelengths of electromagnetic radiation.

For example, in many operations, each surgical tool used during the operation may include an RFID tag. After or during an operation, emitted radio frequencies, in conjunction with an antenna place behind the patient and an RF receiver on an opposing side of the patient, can be used to identify any surgical tools or other instruments still inside the body of the patient before closing of the surgical wound is performed. Typically, the antenna used in such a system is placed underneath a patient lying on the operating table. If a return electrode is needed for performing electrosurgery, the return electrode is placed in direct contact with the patient, and thus between the antenna and the RF receiver. Typically, conductive elements within return electrodes are not transparent to the RF signals so that such a process cannot be used during an operation.

However, the woven fabric material of conductive element 140 of the present disclosure are transparent to such RF imaging systems and other medical imaging systems noted above. For example, in at least one embodiment, the density of conductive element 140 is low enough that RF signals can pass therethrough between the antenna and receiver, but high enough to provide adequate conductive properties necessary to draw current through the body of the patient and into return cable 114. In one or more other embodiments, the thread count and thread thickness of conductive element 104, both of which contribute to the density of conductive element 140, may vary to achieve suitable transparency and conductive properties with a variety of fabric threads and conductive fibers noted above.

Referring still to FIG. 4, disposed on opposing sides of conductive element 140 are pads 142, 144. As can be seen, pad 142 has an outer surface 146 and an inner surface 148. Outer surface 146 is configured to be placed against the surface of a patient (thereby acting as a working surface of return electrode 132), while inner surface 148 is disposed next to conductive element 140. In some embodiments, inner surface 148 is secured to conductive element 140, such as with an adhesive, to prevent air bubbles or separation between pad 142 and conductive element 140. Pad 142 may include outer and inner cover layers that are formed individually and secured together about their edges or are integrally formed. The outer and inner cover layers may define outer and inner surfaces 146, 148. Outer and inner cover layers may be formed of various materials, such as urethane, polyurethane, polyethylene, polypropylene, polyolefins, polyvinyl chloride, PET, etc. A fill material 152, discussed below, may be disposed between the outer and inner cover layers.

Similar to pad 142, pad 144 includes an outer surface 154 and an inner surface 156. Outer surface 154 is configured to be placed on a support surface (e.g., operating table, chair, etc.), while inner surface 156 is disposed next to conductive element 140. Like outer and inner cover layers 146, 148, one or both of outer surface 154 and inner surface 156 may be defined by a cover layer formed of various materials, such as urethane, polyurethane, polyethylene, polypropylene, polyolefins, polyvinyl chloride, PET, etc. Like pad 142, inner surface 156 may be secured to conductive element 140, such as with an adhesive, to prevent air bubbles or separation between pad 144 and conductive element 140. In other embodiments, however, the edges of pad 144 may be secured to the edges of pad 142 with conductive element 140 disposed therebetween. Also like pad 142, pad 144 may include a fill material.

Fill materials used in pads 142, 144 may provide return electrode 132 with some pressure reducing characteristics. More specifically, since pads 142, 144 retain a defined volume of fill material, when an individual rests upon return electrode 132, the fill materials distribute the downward force of the patient throughout the fill materials, thereby decreasing the point forces applied to those parts of the patient's anatomy where bony prominences are located. Nevertheless, as discussed elsewhere herein, pads 142, 144 are relatively thin to ensure sufficient coupling between a patient and conductive element 140. Accordingly, in some situations, such as during lengthy surgical procedures, it may be desirable or necessary to use a separate pressure reducing pad in combination with return electrode 132 to prevent the formation of pressure sores on the patient or to increase the patient's comfort level.

Fill materials used in pads 142, 144 may act as dielectric layers to reduce the current that flows through pads 142, 144, respectively. Alternatively, the fill materials may take the form of conducting materials to aid with the transmission of current therethrough. Additionally, the fill materials may provide a thermal mass for the distribution of heat during an electrosurgical procedure. As discussed above, IEC requires that during an electrosurgical procedure the temperature rise of the patient's tissue should remain below six degrees Celsius (6° C.). The thermal mass provided by the fill materials assists with the distribution of heat throughout the patient's body and substantially eliminates the potential for hot spots that may burn the patient. Consequently, the substances used for fill materials may perform multiple functions during an electrosurgical procedure.

In general, the fill materials may take the form of one or more solids, liquids, gases, or combinations thereof depending on the pressure reducing, dielectric, and/or conducting properties needed for return electrode 132. For example, in one illustrative embodiment, the fill materials are elastomeric gels having low durometer level, such as SORBOTHANE. In addition to SORBOTHANE, various other elastomeric gels may be used, such as but not limited to those based upon the polymer chemistry of urethanes, silicones, hydrophilic elastomers or hydrogels, vinyls, vinyl alcohols, or other similar materials and technologies. Additionally, the fill materials may take the form of water, saline, water based materials, conductive oils, and the like. Still further, the fill materials may take the form of solid but flexible foam-type materials.

The materials forming return electrode 132, conductive element 140, and pads 142, 144, at least partially control the passage of current from a patient to conductive element 140. As such, in one embodiment, pads 142, 144 are insulative. In an alternate configuration, pads 142, 144 may be conductive and aid in the passage of current from the patient to conductive element 140. The various elements of return electrode 132, i.e., conductive element 140 and pads 142, 144, may provide one or more resistive, inductive, and/or capacitive inductance components to the bulk impedance of the return electrode. In this manner return electrode 132 is self-limiting, while also providing at least some pressure reducing characteristics.

In addition to the materials used to form pads 142, 144, the thickness and arrangement of pads 142, 144 and conductive element 140 can affect the transmission of current from a patient to conductive element 140. By way of non-limiting example, the distance between outer surface 146 of pad 142 and conductive element 140 can affect the capacitive coupling between conductive element 140 and a patient resting upon return electrode 132. Through this capacitive coupling, current used during electrosurgery is passed from the patient to return electrode 132. As will be understood by one of ordinary skill in the art in light of the disclosure herein, the capacitive coupling between the patient and return electrode 132 can be directly related to the self-limiting characteristics of return electrode 132. Thus, by changing the distance between the outer surface 146 and the conductive element 140, the capacitive coupling between the patient and the return electrode 132 can be adjusted. Accordingly, as illustrated in FIG. 4, portions of conductive element 140 may be positioned closer to outer surface 146 than other portions of conductive element 140. In other embodiments, conductive element 140 may be spaced a consistent distance from outer surface 146.

Figure 5A:
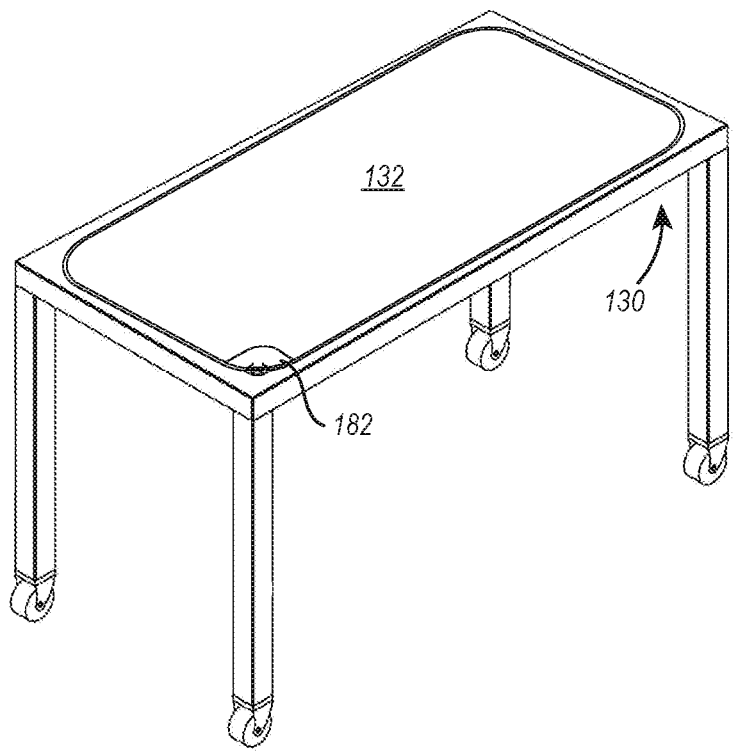
FIG. 5A illustrates an embodiment of a return electrode on an operating table, according to an embodiment of the present disclosure.
Figure 5B:
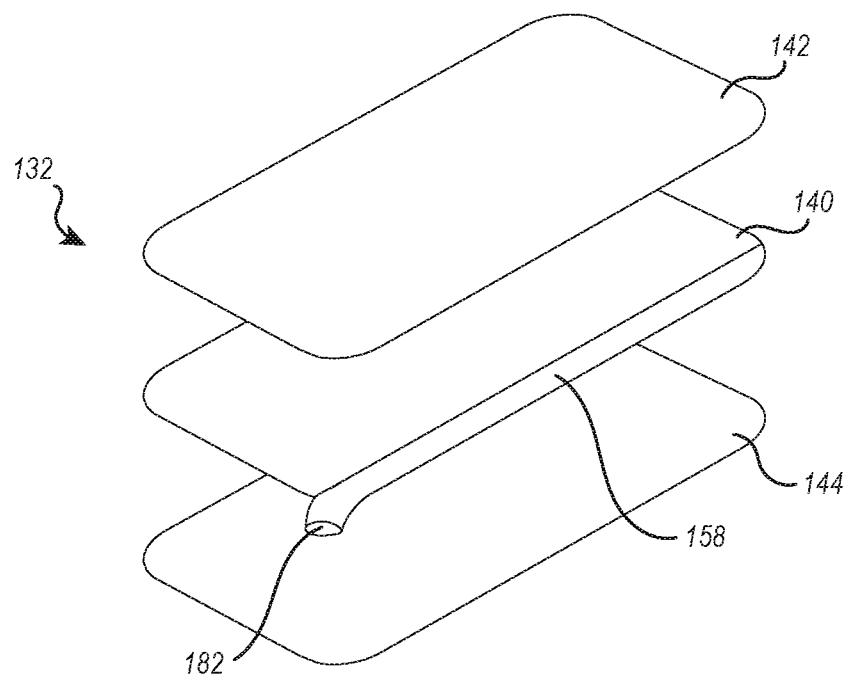
FIG. 5B illustrates an exploded view thereof.

FIG. 5A illustrates return electrode 132 on operating table 130. In at least one embodiment, return electrode 132 includes an electrical connector 182 to provide a conventional electrical return to the electrosurgical radio frequency energy source. As seen in the exploded view of FIG. 5B, conductive element 140, sandwiched between pads 142 and 144, includes bus bar 158 extending along a side edge thereof. Bus bar 158 communicates with electrical connector 182. Conductive fibers of the woven fabric material of conductive element 140 contact bus bar 158 along an edge of conductive element 140 to carry electrical current from conductive element 140 to bus bar 158. Bus bar 158 also serves to reduce the electrical resistance of conductive element 140 to form an electrical connection with return cable 114.

In at least one embodiment, bus bar 158 includes an elongate strip of conductive material disposed along an edge of conductive element 140. In the illustrated embodiment of FIG. 5B, bus bar 158 extends along a long edge of conductive element 140. However, in one or more other embodiments, bus bar 158 extends along a short edge of conductive element 140. In any case, as noted above, bus bar 158 draws electrical current from conductive fibers or threads of the fabric material of conductive element 140 and into electrical connector 182 to be passed through return cable 114.

Bus bar 158 may include any number or combination of conductive materials, including various metals such as gold, silver, nickel, copper, steel, iron, stainless steel, brass, aluminum, or other conductors such as carbon black. In at least one embodiment, bus bar 158 is configured to be flexible along with the fabric material of conductive element 140. In this way, bus bar 158 can be bent and folded along with the rest of conductive element 140 for convenient shipping and storage. The flexibility of bus bar 158 may also reduce the chance of breaking when bent during use. The flexibility of such a bus bar 158 may arise from the material properties thereof, including the thickness and other dimensions of bus bar 158. Also, in at least one embodiment, bus bar 158 is formed as a flexible woven fabric, similar to conductive element 140, including conductive threads or fibers that draw electrical current from the conductive threads or fibers of conductive element 140. The dimensions of bus bar 158, including length, width, and thickness, may also vary in one or more other embodiments from that shown in FIG. 5B.

Figure 6A:
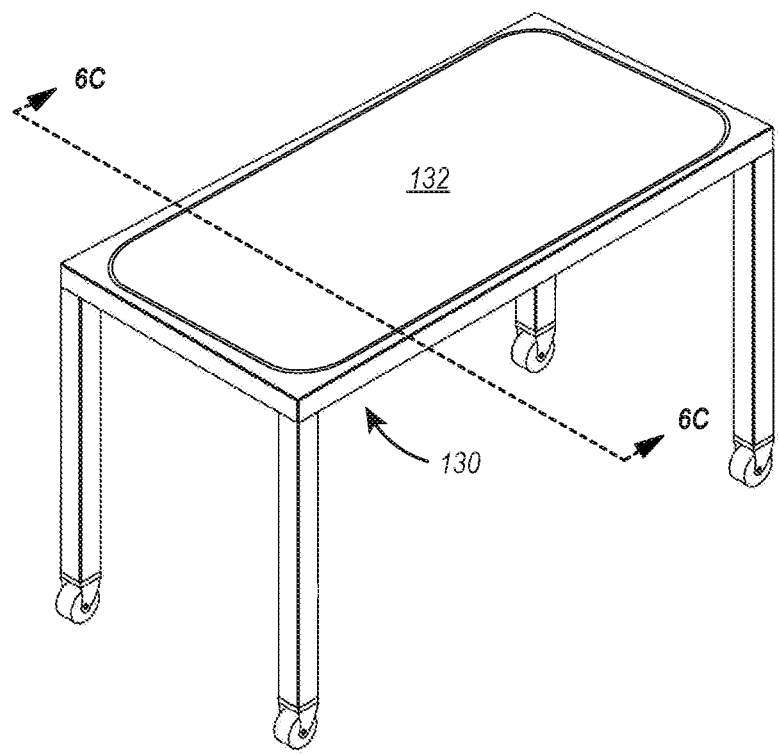
FIG. 6A illustrates an embodiment of return electrode on an operating table, according to an embodiment of the present disclosure.

FIG. 6A illustrates another embodiment of a return electrode 132. In the illustrated embodiment of FIG. 6A, return electrode 132 does not include an exteriorly exposed electrical connection, such as electrical connector 182 shown in FIG. 5A. Rather, as shown in the embodiment of FIG. 6A, return electrode 132 does not include a conventional electrical connection, such as a hard-wired connection or plug anywhere on the return electrode 132. However, as shown in the exploded view of FIG. 6B, conductive element 140 does include bus bar 158, similar to the embodiment of conductive element 140 shown in FIG. 5B.

Embodiments of return electrodes 132 described herein, configured such that no external plug or hard-wired electrical connection is necessary, allow medical personnel to arrange and position the return electrode 132 anywhere within an operating room, regardless of where an electrical outlet or other power source, such as the electrical power generator 100, may be located.

For example, with traditional return electrodes having external plugs or other hard-wired, exposed electrical connections, the electrical plug must be situated within the operating room in a convenient position relative to the power source, such that a power cord can reach between the power source and the return electrode plug without obstructing medical personnel or other medical system during an operation. Thus, external plugs and other hard-wired electrical connections limit the orientations available when setting up the return electrode on an operating table for patient use. The available orientations of return electrodes having external plugs are further limited by the presence of other medical devices and systems connected to the patient, positioned around the operating table, or being used by a doctor or nurse, which power cords and power sources must also accommodate.

In addition to integrating return electrodes having external plugs into existing operating rooms having other devices and systems, other factors further complicate the integration and use of return electrodes having external plugs or other hard-wired electrical connections. For example, medical personnel must take precautions to orient return electrodes having external plugs so that the plug is not in contact with the patient during use, which could cause electrical current to flow back into the patient, causing injury and reducing the effectiveness of the surgical system. Also, for example, medical personnel must take precautions so that the position of the external plug minimizes the chance of fluids entering the plug and disrupting the electrical circuit of the surgical system. All of these factors make it difficult to ensure safe and convenient use of return electrodes having external plugs.

In contrast, and advantageously, return electrodes 132 of the present disclosure that do not include external electrical connectors eliminate the various complications presented by external electrical plugs and other exposed electrical connections by eliminating any external plugs altogether. That is, as shown in FIG. 6A, return electrode 132 includes no such external plugs. Rather, return electrode 132 of FIG. 6A can be oriented and arranged in any configuration within an operating room and underneath a patient without moving the position of the electrical connection between the conductive element 140 and a return cable 114.

In order to draw electrical current from bus bar 158 of a conductive element 140 having no externally exposed connectors, at least one embodiment of an electrosurgical system comprises a capacitive electrical connection between conductive element 140 of return electrode 132 and return cable 114. The capacitive connection can occur anywhere along the edge of return electrode 132 where bus bar 158 is positioned.

Figure 6B:
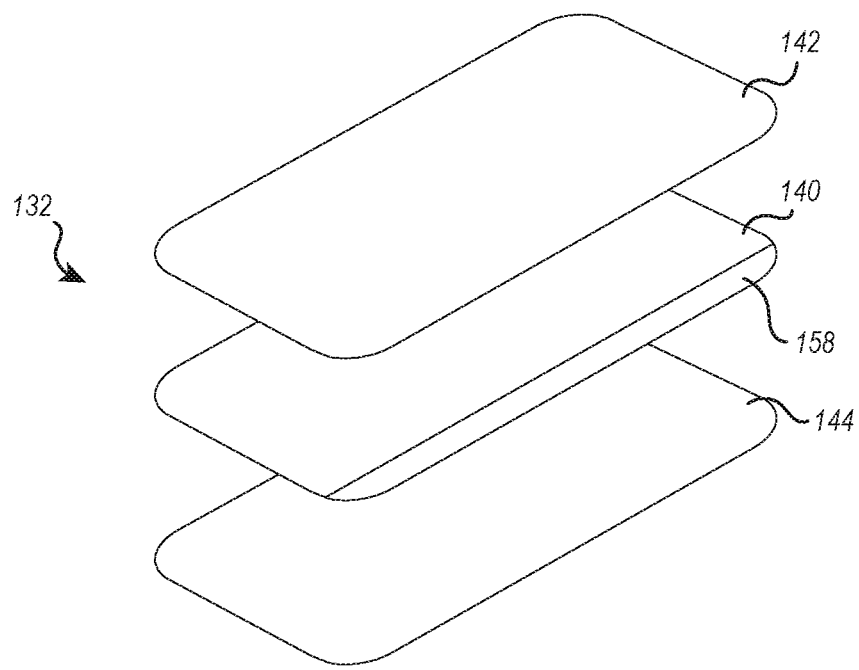
FIG. 6B illustrates an exploded view thereof.

As seen in the exploded view of FIG. 6B, and inferred in FIG. 6A, conductive element 140 is sandwiched between pads 142 and 144. In at least one embodiment, pads 142 and 144 of the return electrode 132 completely encompass conductive element 140, which is disposed completely within the return electrode 132 so that no portion of conductive element 140, including bus bar 158, is exposed or accessible from outside return electrode 132.

In such an embodiment, return electrode 132 includes a simplified geometry without hard-to-reach contours and recesses of an externally exposed electrical plug or other common electrical connection. This is advantageous when cleaning and/or sterilizing return electrode 132 between patient uses to reduce the risk of infections. For example, typical return electrodes include an electrical connection or plug in communication with the conductive heating element inside the return electrode. During sterilization with wipes or other common sterilization techniques, it can be difficult for medical personnel to reach the inside contours and crevasses of the electrical connection. As such, bacteria may remain within the connection. In contrast, return electrodes 132 of the present disclosure do not include such common connections. As a result, return electrode 132 can more easily be thoroughly wiped and disinfected between uses, reducing the risk of infection to the patients laying thereon.

In addition, the material of the conductive element inside return electrode 132 is not exposed in any way to be corroded, damaged, or otherwise harmed when shipped, moved, stored, and used. No electrical connection is present to break or corrode. Also, the return electrode may be freely folded, rolled, or otherwise packaged and stored in any number of ways without rigid or bulky electrical connections getting in the way or complicating packaging or storing processes.

To illustrate the construction of at least one embodiment of return electrode 132, including conductive element 140 and bus bar 158 disposed therein, FIG. 6C illustrates a simplified section taken along the lines 6C-6C of FIG. 6A and FIG. 6D illustrates an exploded section view of return electrode 132. As illustrated in FIGS. 6C and 6D, return electrode 132 includes conductive element 140 and pads 142, 144 on opposing sides of conductive element 140. Pads 142, 144 may be referred to individually as upper pad 142 and lower pad 144. However, as will be clear from subsequent descriptions and figures, either pad 142 or 144 may be oriented above or below conductive element 140 during use while maintaining the functionality of return electrode 132. Indeed, at least one advantage of return electrode 132 is that medical personnel can place return electrode 132 in any orientation on operating table 130 without losing functionality provided by return electrode 132.

Disposed on opposing sides of conductive element 140 are pads 142, 144. As can be seen, pad 142 has an outer cover layer 160 and an inner cover layer 162 that define an interior chamber 164 therebetween. Outer cover layer 160 is configured to be placed against the surface of a patient (thereby acting as a working surface of return electrode 132), while inner cover layer 162 is disposed next to conductive element 140. In some embodiments, inner cover layer 162 is secured to conductive element 140, such as with an adhesive, to prevent air bubbles or separation between pad 142 and conductive element 140. Outer and inner cover layers 160, 162 may be formed individually and secured together about their edges or may be integrally formed. Outer and inner cover layers 160, 162 may be formed of various materials, such as urethane, polyurethane, polyethylene, polypropylene, polyolefins, polyvinyl chloride, PET, etc. A fill material 166, similar to that discussed elsewhere herein, may be disposed in interior chamber 164.

Similar to pad 142, pad 144 includes an outer cover layer 168 and a fill material 170. Outer cover layer 168 is configured to be placed against the surface of a patient (thereby acting as a second working surface of return electrode 132), while fill material 170 is disposed next to conductive element 140. Like outer and inner cover layers 160, 162, outer cover layer 168 may be formed of various materials, such as urethane, polyurethane, polyethylene, polypropylene, polyolefins, polyvinyl chloride, PET, etc.

Rather than having a second inner cover layer, pad 144 may be formed during the assembly of return electrode 132. For instance, during assembly of return electrode 132, chamber 164 in pad 142 may be filled with material 166 and sealed closed such that material 166 cannot escape from chamber 164. Pad 142 may be disposed next to and/or secured to a first major surface of conductive element 140. The edges of outer cover layer 168 may then be secured to the edges of pad 142 so as to create a chamber between conductive element 140 and outer cover layer 168. The newly defined chamber may then be filled with material 170 and sealed closed to retain material 170 therein.

It will be appreciated that pads 142, 144 may be similar or identical to one another. For instance, in addition to outer cover layer 168 and material 170, pad 144 may also include an inner cover layer (similar to inner cover layer 162) that cooperates with outer cover layer 168 to define a chamber for receiving material 170. Furthermore, pad 144 may also be at least partially secured to conductive element 140. For instance, in embodiments where pad 144 includes an inner cover layer, the inner cover layer may be secured, such as with an adhesive, to a second major surface of conductive element 140.

Likewise, pad 142 may be similar to pad 144 in that pad 142 may be formed without inner cover layer 162. In such an embodiment, the outer layer 160 of pad 142 may be secured to outer layer 168 of pad 144. Additionally, or alternatively, in at least one embodiment, each outer layer 160, 168 may at least partially secure to the conductive element 140, for example at an outer edge thereof, as well as to the opposing outer layer 160, 168.

In any case, one will appreciate that conductive element 140 of return electrode 132 is completely encompassed by the surrounding pads 142, 144 so that conductive element 140 is not exteriorly exposed in any way, as shown in the embodiment of return electrode 132 illustrated in FIGS. 6A and 6B.

While FIG. 6C illustrates a cross-sectional view of return electrode 132 taken along lines 6C-6C in FIG. 6A, the cross-sectional view of return electrode 132 would look similar regardless of the orientation of the line 6C-6C, whether it be longitudinal, lateral, or diagonally disposed across return electrode 132. That is, the pads 142, 144 extend beyond the outer edges of conductive element 140 around the entire perimeter of return electrode 132 so that the conductive element is disposed within, and completely encompassed by, pads 142, 144.

In at least one embodiment, pads 142, 144 are welded, adhered, sealed, or otherwise formed together at a pad juncture 172 around the outer perimeter of conductive element 140. In at least one embodiment, pads 142, 144 are integrally formed together as a single piece. In any case, as noted above, conductive element 140 is completely surrounded and encompassed by pads 142, 144 so that no portion of conductive element 140 is exposed or extending beyond pads 142, 144. Furthermore, as noted above with reference to FIG. 6A, there is no conductive electrical plug or any other external conductive electrical connection that passes through pad juncture 172 at any point around the perimeter of return electrode 132 to make conductive electrical contact with the conductive element 140. Conductive element 140 is thus completely isolated from the environment outside of pads 142, 144.

The materials forming return electrode 132, conductive element 140, and pads 142, 144, control the passage of current from a patient to conductive element 140. As such, in at least one embodiment, pads 142, 144 and fill materials 166, 170 are insulative, while, in an alternate configuration, pads 142, 144 and/or materials 166, 170 may be conductive and aid in the passage of current from the patient to conductive element 140. The various elements of return electrode 132, i.e., conductive element 140 and pads 142, 144, may provide one or more resistive, inductive, and/or capacitive inductance components to the bulk impedance.

In addition to the materials used to form pads 142, 144, the thickness of pads 142, 144 can affect the transmission of current from a patient to conductive element 140. By way of non-limiting example, forming pads 142, 144 relatively thin can facilitate capacitive coupling between conductive element 140 and a patient resting upon return electrode 132. Through this capacitive coupling, current used during electrosurgery is passed from the patient to return electrode 132. As will be understood by one of ordinary skill in the art in light of the present disclosure, the capacitive coupling between the patient and return electrode 132 can be directly related to the self-limiting characteristics of return electrode 132. Thus, making pads 142, 144 relatively thin contributes to good electrical coupling between the patient and return electrode 132 so as to enable safe and effective electrosurgery for substantially any sized patient. Accordingly, one or both of pads 142, 144 may have a thickness within a predetermined range.

For instance, in some embodiments, one or both of pads 142, 144 has an approximate thickness of between about 0.02 inches and about 0.120 inches. In other embodiments, one or both of pads 142, 144 has an approximate thickness of less than about 0.10 inches, about 0.09 inches, about 0.075 inches, about 0.06 inches, about 0.05 inches, about 0.03 inches, or about 0.02 inches. In some embodiments, return electrode 132 has a total thickness of about 0.135 inches or less.

The inclusion of pads 142, 144, which are substantially similar to one another, on opposing sides of conductive element 140 provides return electrode 132 with a substantially symmetrical construction. The symmetrical nature of return electrode 132 provides return electrode 132 with two surfaces that function as working surfaces. More specifically, the major surfaces of return electrode 132 defined by outer cover layers 162, 168 may each be used as a working surface. For instance, return electrode may be positioned so that outer cover layer 162 is positioned towards a patient and return electrode 132 will exhibit the self-limiting characteristics discussed herein. Likewise, return electrode 132 can be turned over so that outer cover layer 168 is positioned against a patient and return electrode 132 will exhibit the self-limiting characteristics discussed herein.

As noted above with reference to FIG. 2, an electrical return cable 114 may be connected to return electrode 132 to carry electrical current back to electrical power generator 100, thus drawing current out from the patient via return electrode 132. Accordingly, electrosurgical systems incorporating the various embodiments of return electrodes 132, 174 described herein may employ one or more capacitive electrical connections that allow current to pass through at least pads 142, 144 surrounding conductive element 140, or any other materials separating conductive element 140 from return cable 114.

In at least one embodiment, the capacitive connection between return cable 114 and conductive element 140 may include a conductive material removably secured to return electrode 132. Such removable connections may be accomplished using magnetic connections, pressure adhesive connections, hook-and-loop connections, spring loaded clips, or other removable means to secure a conductive material to return electrode 132. In at least one embodiment, a capacitive connection may include a conductive material placed underneath return electrode 132 such that the weight of a patient secures the capacitive connection against return electrode 132 between return electrode 132 and operating table 130. Other capacitive connections are also contemplated herein, which bring a conductive material in close enough proximity to bus bar 158 that current can pass from bus bar 158 to the conductive material, which is electrically connected to return cable 114.

Embodiments of return electrodes described thus far, including those shown in FIGS. 2-6D, are configured as generally flat, laminar pads that may be placed on an operating table during use. In such embodiments, as noted above, contact between the patient and return electrode 132 arises from the weight of the patient pushing down on return electrode 132 against operating table 130. Due to the potential movement and repositioning of a patient's body during an operation, and the curvilinear contours of a patient's body, such contact can be unreliable and unpredictable, potentially affecting the proper functioning of return electrode 132 and thus the entire electrosurgical system.

In order to ensure a proper, consistent, and secure connection between a patient and a return electrode during an operation, regardless of patient body geometry and repositioning or movement thereof during an operation, at least one embodiment of return electrode 174 includes a wearable return electrode 174. Such an embodiment is illustrated in FIG. 7A. Here, return electrode 174 includes a flexible, sheath-type structure configured to be placed over a limb or other body part of a patient. Return electrode 174 is shown as a hollow, cylindrical sheath in FIG. 7A. However, return electrode 174 is flexible so that it can conform to the contours of the body of the patient wearing return electrode 174. As will be noted below with reference to subsequent figures, return electrode 174 may take many different forms such that return electrode 174 can be worn by a patient over a variety of areas of the body.

FIG. 7B illustrates an exploded view of return electrode 174 of FIG. 7A, including pad 142, conductive element 140, and pad 144. Conductive element 140 includes bus bar 158 and conductive element 140 may be comprised of conductive fabric fibers and/or threads woven together as described above. Bus bar 158 may also comprise various conductive materials and/or fabrics as noted above. In addition, pads 142, 144 may comprise materials, layers, and configurations described above with regard other pads 142, 144 found in FIGS. 4-6D. In addition, pads 142, 144 and conductive element 140 may be combined as shown in FIG. 7A such that conductive element 140 is completely encompassed by pads 142, 144, without any externally exposed electrical connections, as described above. Alternatively, at least one embodiment of return electrode 174 may include an external electrical connector, similar to electrical connector 182 shown in FIGS. 5A and 5B.

Figure 7C:
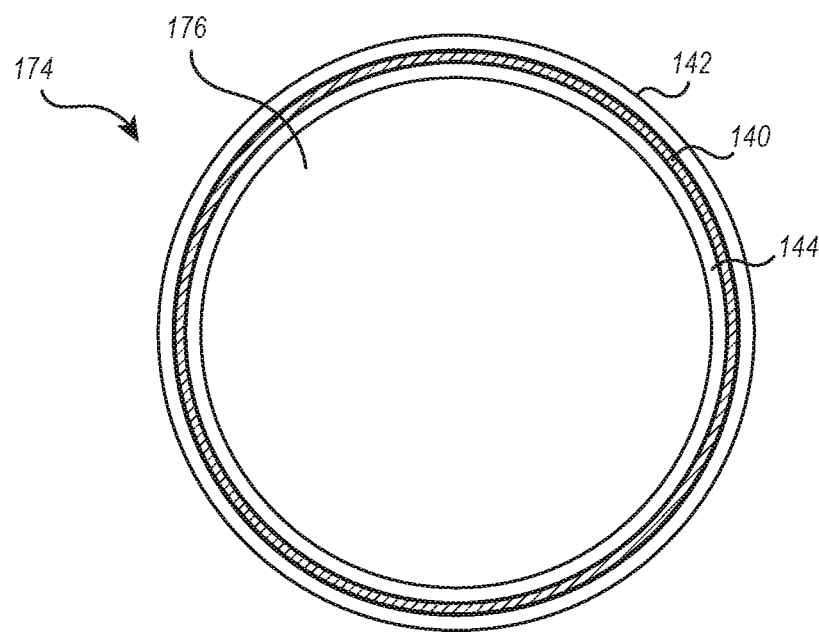
FIG. 7C illustrates a cross-sectional view of the return electrode illustrated in FIG. 7A, taken along the plane 7C indicated in FIG. 7A.

As seen by the cross-sectional view of FIG. 7C, taken along line 7C-7C of FIG. 7A, conductive element 140 is sandwiched between pads 142, 144. In such a wearable configuration, pad 144 serves as an inner pad defining a passageway 176 and pad 142 serves as an outer pad. In at least one embodiment, the materials of pads 142, 144 and conductive element 140 are flexible and elastic to conform to a patient's contours when worn. More details regarding the patient wearing such a return electrode is given hereafter with reference to FIGS. 9 and 10.

Figure 7D:
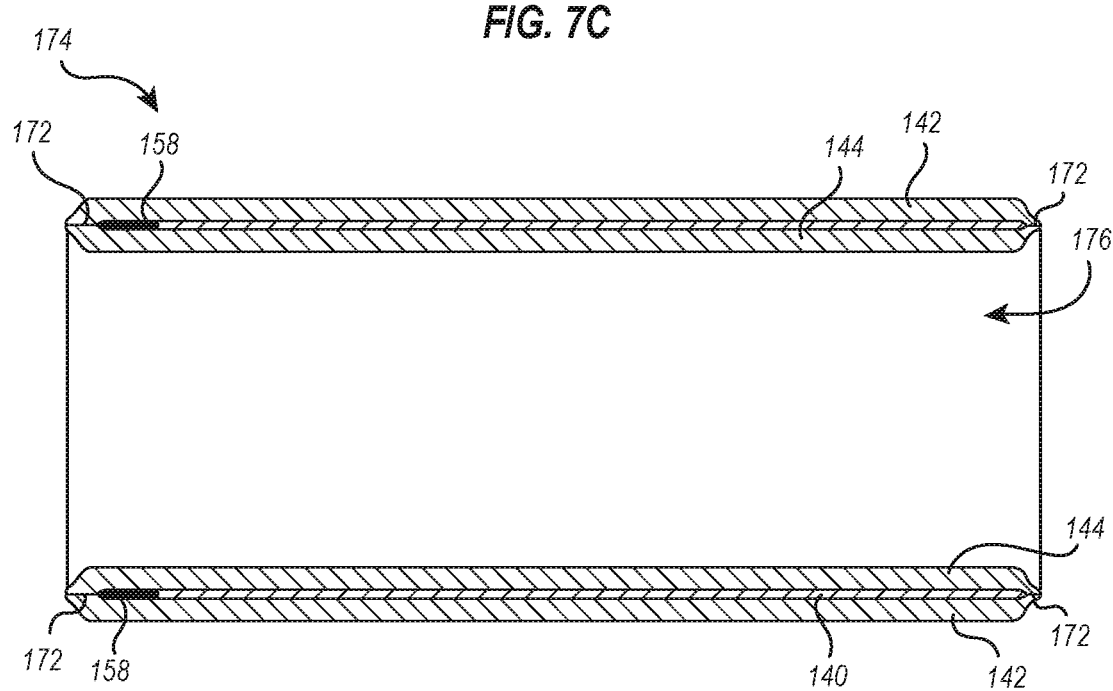
FIG. 7D illustrates a cross-sectional view of the return electrode illustrated in FIG. 7A, taken along the plane 7D indicated in FIG. 7A.

First, with reference to FIG. 7D, at least one embodiment of return electrode 174 includes conductive element 140 sandwiched between outer pad 142 and inner pad 144. As noted previously, pads 142, 144 may be brought together at pad juncture 172 to secure conductive element 140 therebetween. Pads 142, 144 may be permanently secured together at pad juncture 172 or they may be removably secured together at pad juncture 172, such as by pressure adhesives, hook-and-loop material, zippers, snaps, or the like. Alternatively, in at least one embodiment, pads 142, 144 may not be secured together at pad juncture 172. Rather, each layer of return electrode 174, including pads 142, 144 and conductive element 140 may be separately donned over the limb or other body part of a patient.

In addition, at least one embodiment of return electrode 174 may not include all layers, including pads 142, 144 and conductive element 140. For example, in at least one embodiment, return electrode 174 may only include conductive element 140 and outer pad 142. In such an embodiment, return electrode 174 may include a flexible, fabric conductive element 140 placed over/around a portion of the patient and an outer pad 142 placed over and around conductive element 140. In such an embodiment, outer pad 142 may act as a compression layer that holds conductive element 140 to the patient. Additionally, or alternatively, return electrode 174 may include additional layers not shown in the figures. For example, an embodiment of return electrode 174 that includes all layers, including pads 142, 144 and conductive element 140, may also include an additional outer cover layer that extends over return electrode 174 to secure return electrode 174 to the patient.

Figure 8A:
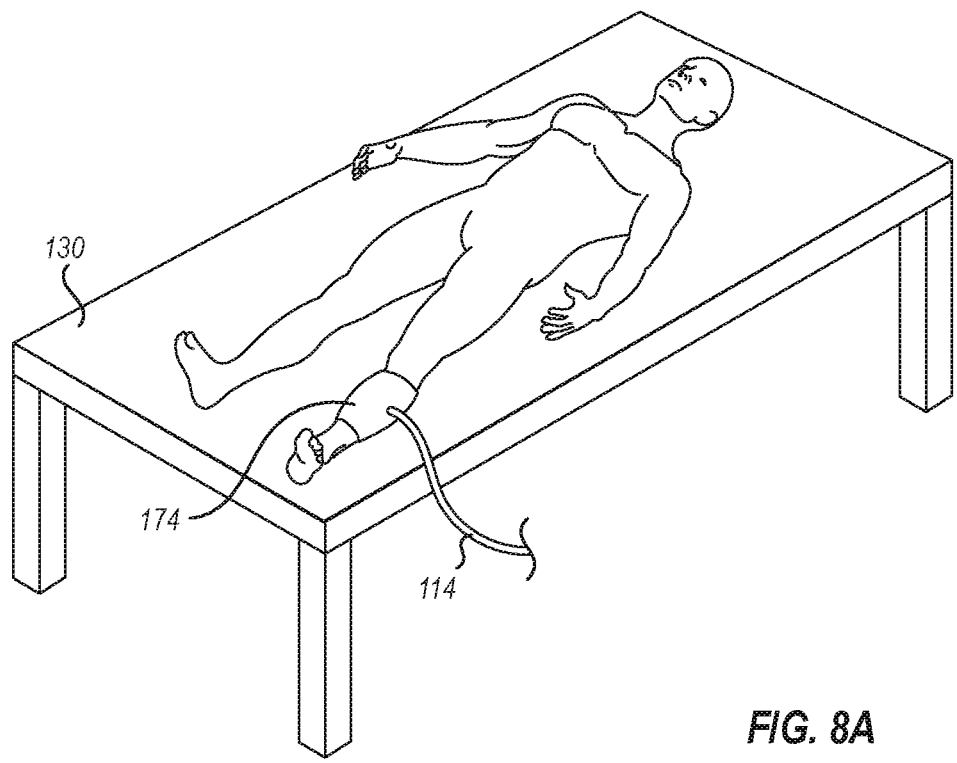
FIG. 8A illustrates an embodiment of a return electrode secured to a patient, according to the present disclosure.

Along these lines, FIG. 8A illustrates return electrode 174 secured to a patient lying on operating table 130. In the illustrated implementation of return electrode 174 return electrode 174 is secured around a lower leg portion of the patient. Return cable 114 extends from return electrode 174. As noted above, in at least one embodiment, return electrode 174 is flexible and elastic so that return electrode 174 conforms to the contours of the patient's body, in this case the contours of the lower leg of the patient. In such an embodiment, return electrode 174 may be expanded to fit over the leg or foot of the patient and then the elasticity of return electrode 174, or the various layers thereof, including pads 142, 144 and conductive element 140, hugs the leg of the patient to secure return electrode 174 thereto via friction fit. In this sense, return electrode 174 is wearable over the limbs or other portions of the patient's body.

In such an embodiment shown in FIG. 8, bus bar 158 of return electrode 174 is held in close contact with the patient along with conductive element 140. In order to prevent electrical current, which flows through the body of the patient during an electrosurgical operation, from predominantly flowing directly into bus bar 158 and burning the patient as electrical current concentrates only in bus bar 158, instead of spreading out and flowing through the fabric portion of conductive element 140, bus bar 158 may include one or more insulating features. For example, as seen in FIG.

8B, at least one embodiment of conductive element 140 includes an insulating layer 178 at least partially surrounding bus bar 158.

In at least one embodiment, insulating layer 178 may include a separate layer surrounding bus bar 158. Alternatively, or additionally, insulating layer 178 may comprise a coating layer that coats bus bar 158. Insulating layer 178 prevents electrical current flowing through the patient's body from entering directly into bus bar 158. In at least one embodiment, a portion of bus bar 158 may remain uninsulated to enable an electrical connection with return cable 114. In embodiments where conductive element 140 includes an externally exposed electrical connector, such as electrical connector 182 shown in FIGS. 5A and 5B, bus bar 158 may be entirely coated or covered with insulating layer 178 and an electrical connector may pierce through insulating layer 178 to make direct electrical contact with bus bar 158.

Figure 8B:
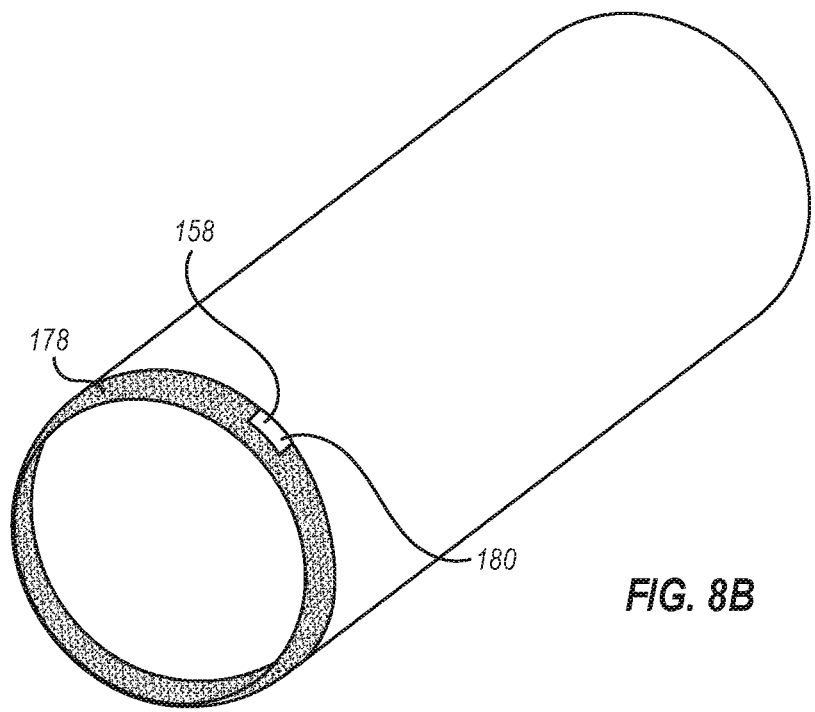
FIG. 8B illustrates an embodiment of a return electrode, according to the present disclosure.
Figure 8C:
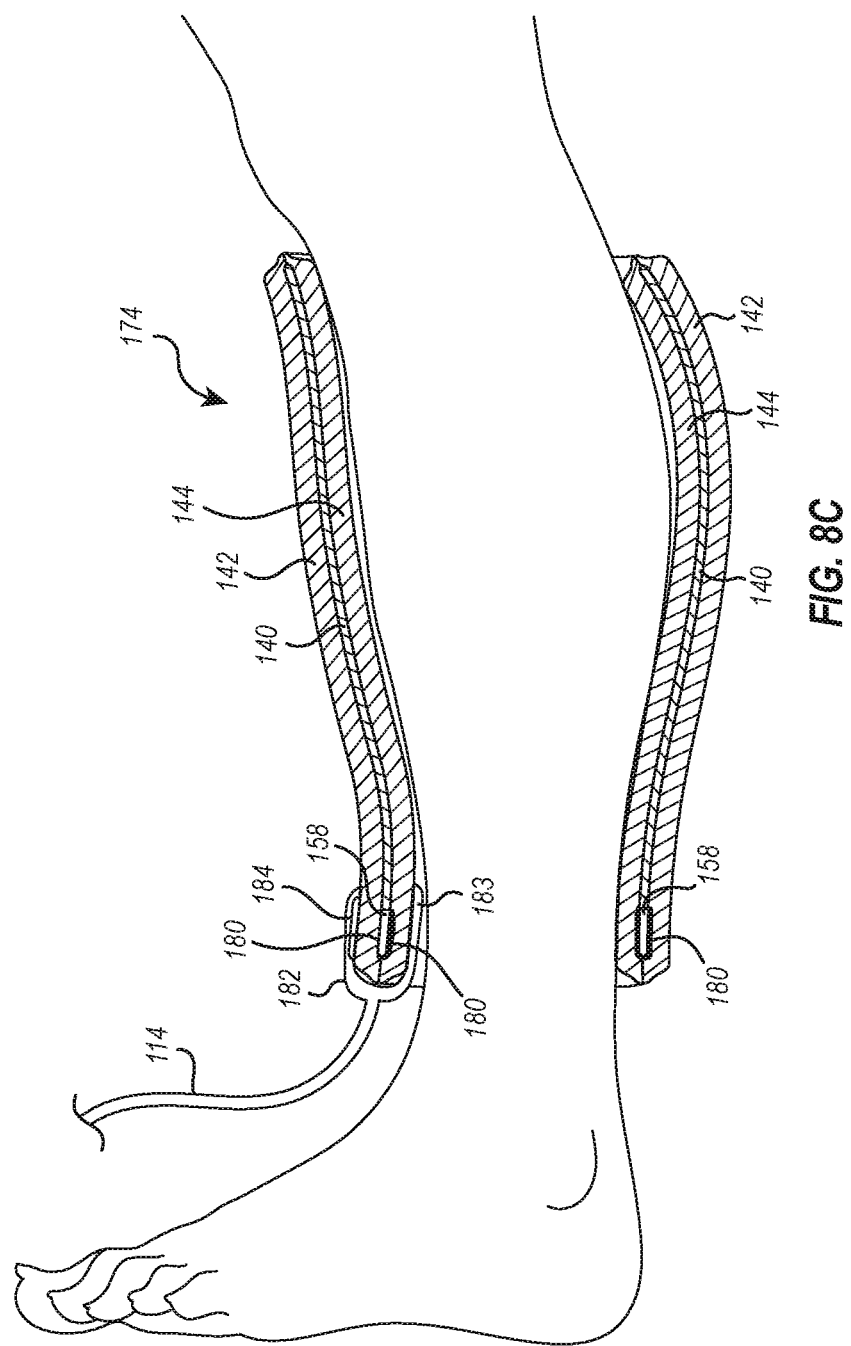
FIG. 8C illustrates an embodiment of a return electrode secured to a patient, according to the present disclosure.

Alternatively, in embodiments where conductive element 140 does not include any externally exposed electrical connector, such as the embodiment illustrated in FIG. 7D, one or more portions of bus bar 158 may remain exposed with no insulating layer 178, such as exposed layer 180 illustrated in FIG. 8B. In such an embodiment, the exposed portion 180 may remain available to make a capacitive connection with a capacitive connector secured exteriorly to return electrode 174. Such an embodiment is illustrated in FIGS. 8B and 8C. The number, location, and size of exposed portions 180 may vary in different embodiments.

Along these lines, FIG. 8C illustrates a cross-sectional view of return electrode 174 secured over the lower leg of a patient. A capacitive connector 182 may include a clamp that positions a conductive portion 184 in close enough proximity to bus bar 158 to create a capacitive electrical connection therebetween. In such an embodiment, bus bar 158 may be void of an insulating layer 178 between bus bar 158 and conductive portion 184 to enable the connection. The remainder of bus bar 158 may include insulating layer 178, as shown between bus bar 158 and the upper side of the leg of the patient and around bus bar 158 portions situated underneath the leg or otherwise not in the vicinity of conductive portion 184 of capacitive connector 182. Again, insulating layer 178 protects the patient by preventing the concentration of electrical current flowing directly into bus bar 158. Because insulating layer 178 surrounds bus bar 158, current flowing through the leg of the patient will first enter and spread out through conductive element 140 and then travel to bus bar 158 outside the body.

Alternatively, or additionally, exposed portion 180 may extend below bus bar 158 so that no insulating layer 178 is positioned between bus bar 158 and the leg of the patient at exposed portion 180. In such an embodiment, a lower arm 183 of capacitive connector 182 may serve as an insulator to prevent electrical current from flowing directly from the leg of the patient to bus bar 158 at exposed portion 178.

In addition, insulating layer 117 may be included within or as a part of portions of pads 142, 144 that surround conductive element 140 and bus bar 158. In such an embodiment, insulating layer 178 may be integrated into pads 142, 144 or portions of pads 142, 144 surrounding bus bar 158. Additionally, in at least one embodiment, pads 142, 144 may be doped with insulating material at locations surrounding bus bar 158, as described above.

Because conductive element 140 and bus bar 158 may not be visible, as they are sandwiched between pads 142, 144, exterior surfaces of pads 142, 144 may include one or more visual indicators indicating the position of the exposed portion of bus bar 158. In this way, the visual indicators can show where to place capacitive connector 182 on return electrode 174 to form a capacitive connection between bus bar 158 and capacitive connector 182. The foregoing insulating layer 178 described with respect to embodiments of return electrode 174 illustrated in FIGS. 7A-8C can also be applied to other embodiments of return electrodes described herein, whether wearable or not.

Figure 9:
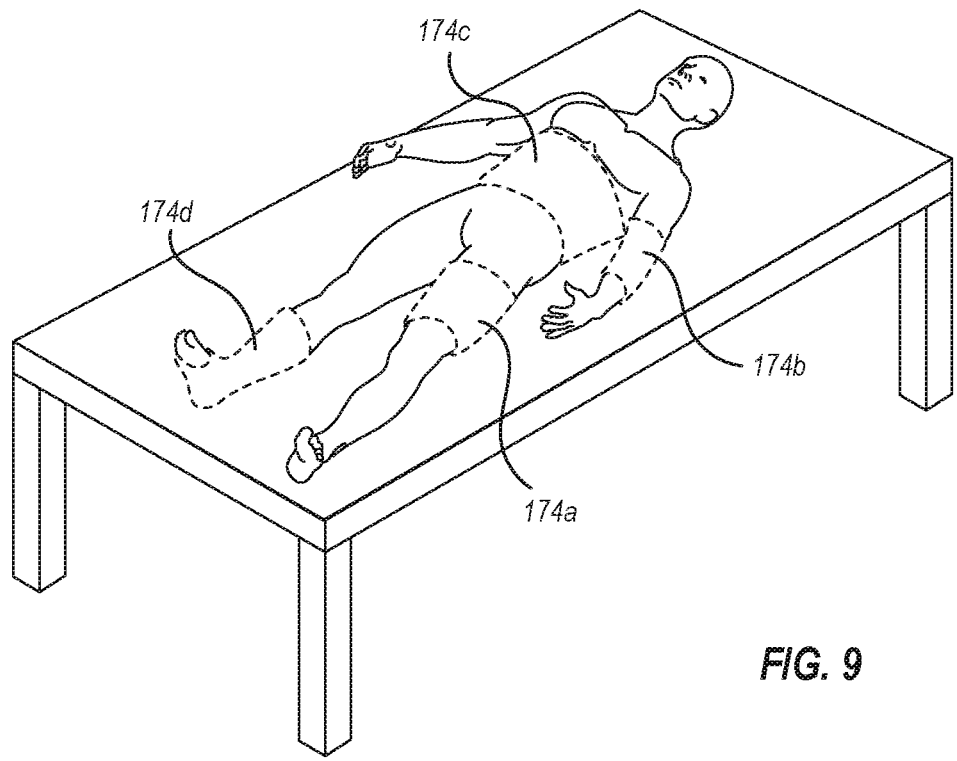
FIG. 9 illustrates various embodiments of return electrodes secured to a patient, according to the present disclosure.

FIG. 9 illustrates possible positions of return electrodes 174*a*-*d* on the body of a patient, including the upper leg 174*a*, arm 174*b*, torso 174*c*, and lower foot and ankle 174*d*. One will appreciate that the size and shape of return electrode 174 can vary depending on where return electrode 174 is placed on the body of a patient. In addition, in at least one embodiment, return electrode 174 may be closed at one end to form a sock or glove-type structure that may also be donned by the patient. Additionally, or alternatively, as noted above, return electrode 174 may also include additional outer cover layers, whether fabric or not, that extend over return electrode 174 to hold return electrode 174 over the body of the patient. Such outer covers may also be water resistant to prevent return electrode 174 from getting wet during an operation. Materials of such outer covers may be similar to materials described with reference to pads 142, 144 described herein.

The configuration, size, shape, and placement of return electrode 174 may thus vary depending on the needs of a particular operation. For example, it is advantageous to don return electrode 174 over the torso of a patient if the operation is performed on the leg. Conversely, during operations on the torso of a patient, it may be advantageous to place return electrode 174 over a peripheral limb of the patient so as not to get in the way of the operation.

Likewise, the extent to which return electrode 174 covers and contacts the surface area of a patient may also vary in other embodiments. For example, in at least one embodiment, return electrode 174 may take the form of pants that cover all of a patient from the waist down. Alternatively, or additionally, return electrode 174 may take the form of a shirt that covers the torso and at least a portion of the arms of a patient. One will appreciate from the foregoing that return electrode 174 can take many forms, shapes, and configurations in order to allow a patient to wear return electrode 174 and make sufficient contact therewith to enable the flow of electrical current out of the patient and into conductive element 140.

Figure 10A:
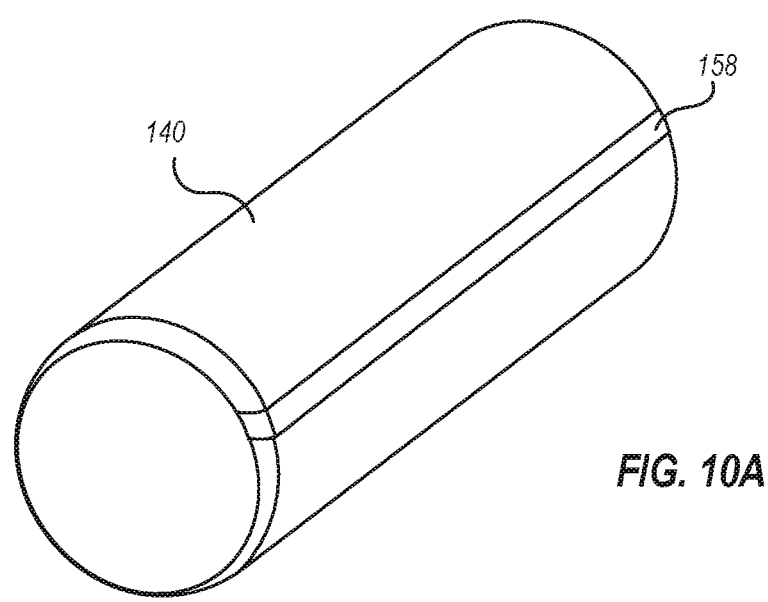
FIG. 10A illustrates an embodiment of a return electrode, according to the present disclosure.
Figure 10B:
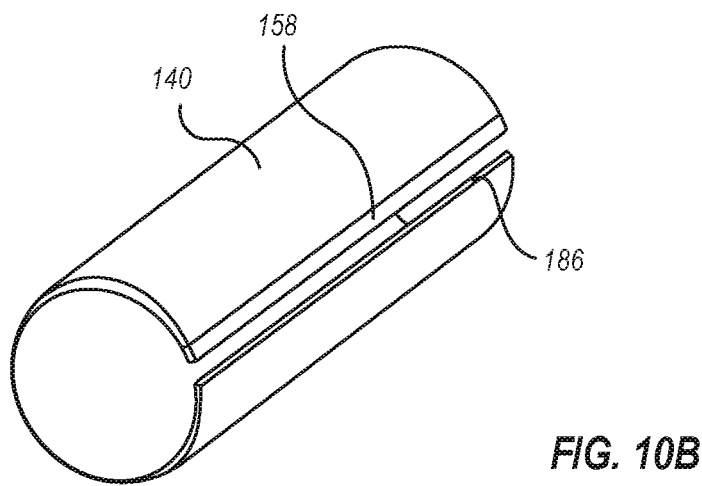
FIG. 10B illustrates an embodiment of a return electrode, according to the present disclosure.
Figure 10C:
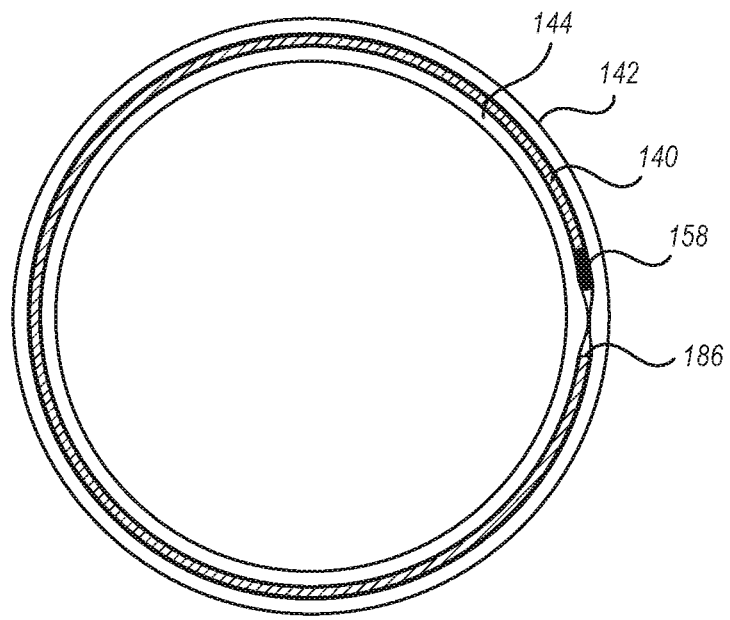
FIG. 10C illustrates a cross-sectional view thereof.

Attention is now directed to FIGS. 10A-10C, which illustrate another embodiment of conductive element 140 disposed in return electrode 174. FIG. 10A illustrates conductive element 140 having bus bar 158 extending longitudinally along conductive element 140. In such a configuration, bus bar 158 may also be insulated by insulating layer 178 as described above with reference to other embodiments. In the illustrated embodiment of FIG. 10A, electrical current entering conductive element 140 may flow through the conductive fibers/threads of conductive element 140 and to bus bar 158 in any direction. Alternatively, as shown in FIG. 10B, conductive element 140 may include a longitudinally extending bus bar 158 and a gap between one side of bus bar 158 and an opposing edge 186 of conductive element 140. In this embodiment, electrical current entering conductive fabric of conductive element 140 can only flow one direction into bus bar 158.

Figure 10D:
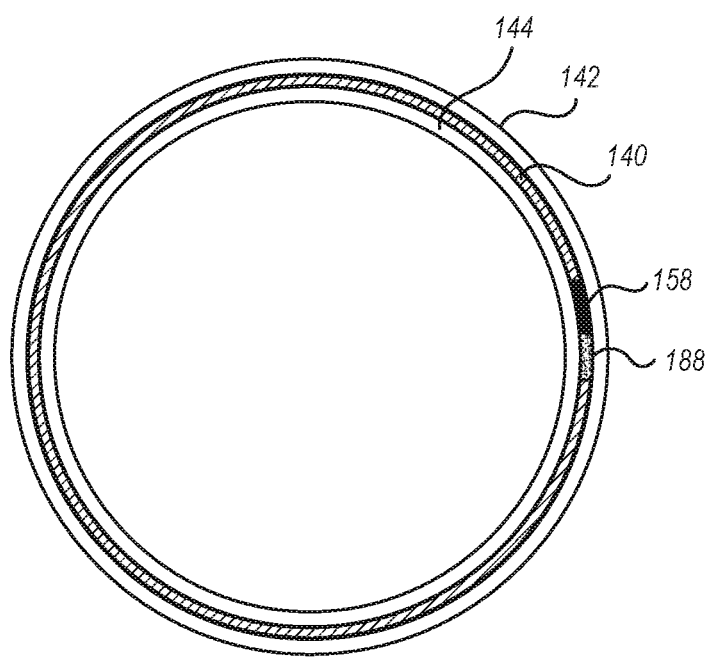
FIG. 10D illustrates another cross-sectional view thereof.

FIGS. 10C and 10D illustrate how such a gap may be filled when conductive element 140 is sandwiched between pads 142, 144 during use. As shown in FIG. 10C, a gap between bus bar 158 and opposing edge 186 of conductive element 140 is filled by opposing pads 142, 144 which fill the gap when conductive element 140 is sandwiched therebetween. Alternatively, as illustrated in FIG. 10D, the gap may be filled with an insulating material portion 188. The insulating material portion 188 may be formed with conductive element 140 or separately inserted in the gap when conductive element 140 is sandwiched between pads 142, 144.

Figure 11A:
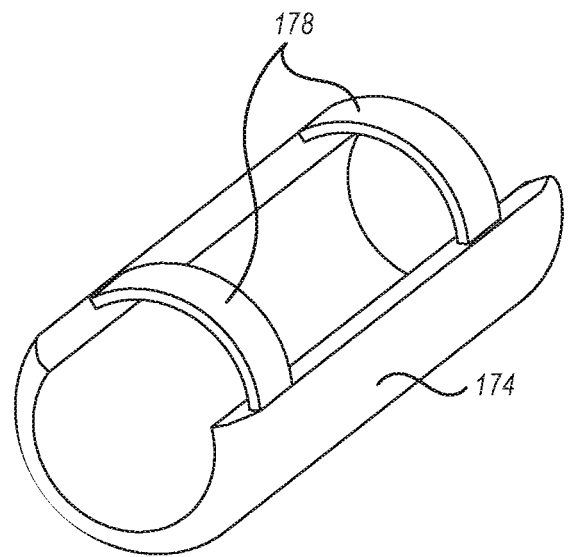
FIG. 11A illustrates an embodiment of a return electrode, according to the present disclosure.
Figure 11B:
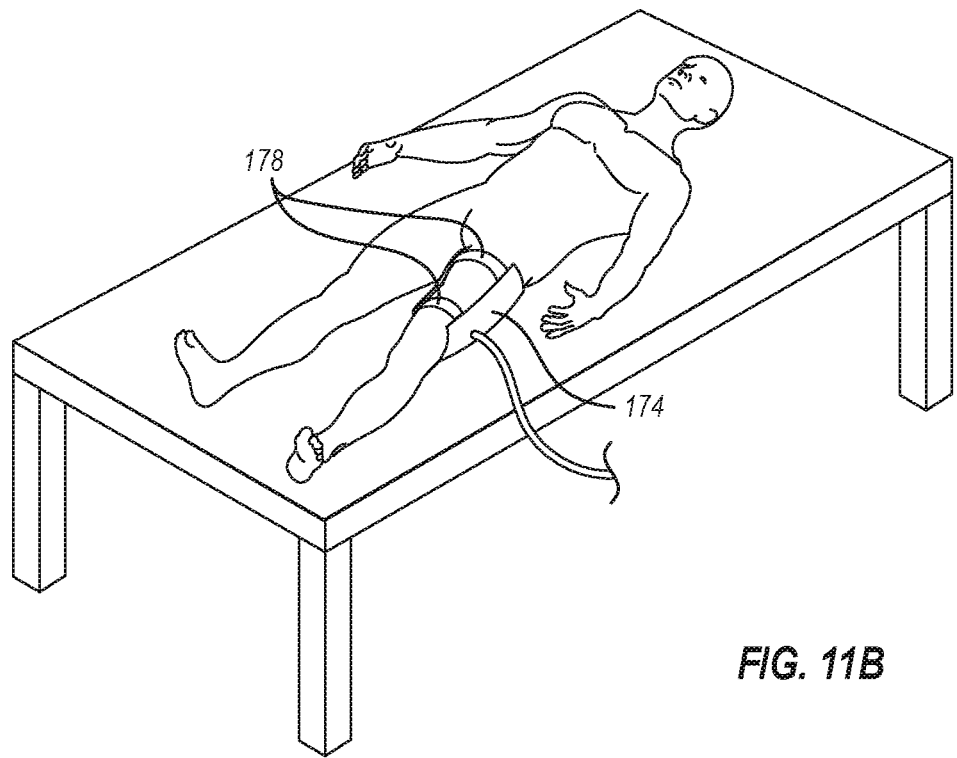
FIG. 11B illustrates the return electrode illustrated in FIG. 11A secured to a patient.

In addition to the foregoing, one or more embodiments of return electrode 174 may also include straps or other securement means to secure return electrode 174 to the body or portion of the body of a patient. For example, FIG. 11A illustrates return electrode 174 including securement straps 178 that hold return electrode 174 to the patient, as seen in FIG. 11B. In such an embodiment, return electrode 174 may not extend completely around a limb or other portion of the body of the patient. In at least one embodiment, straps 178 are flexible and elastic so that straps 178 secure return electrode 174 over a leg or other portion of the patient. In at least one embodiment, straps 178 are permanently secured to return electrode 174. In at least one embodiment, straps 178 are removably secured thereto, at one or both ends thereof, such that they may be removed. In at least one embodiment, straps 178 comprise adjustability features, for example a belt system having a buckle and belt holes, or other adjustable strap mechanisms known in the art. In such an embodiment, straps 178 can be loosened to fit return electrode 174 over a portion of the body of the patient and then tightened to secure return electrode 174 to the patient.

Figure 12:
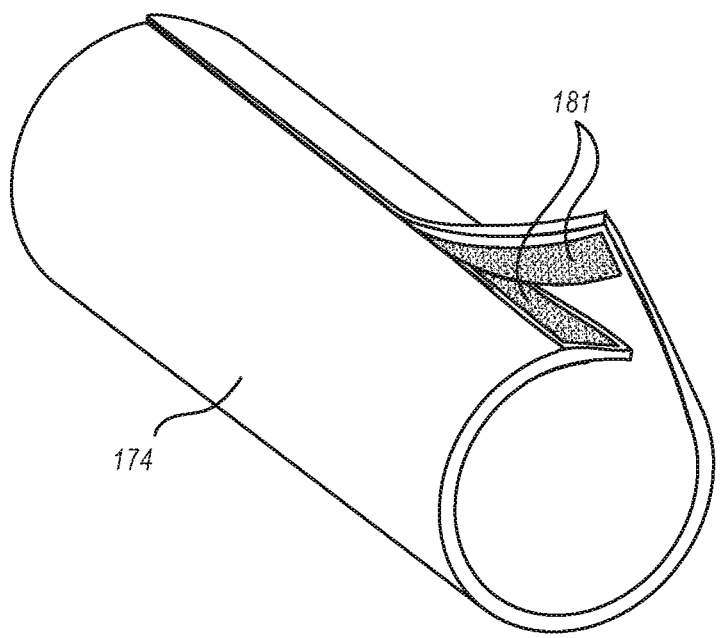
FIG. 12 illustrates an embodiment of a return electrode, according to the present disclosure.

Alternatively, or additionally, as shown in FIG. 12, at least one embodiment of return electrode 174 can include hook-and-loop portions 181 on opposing edges thereof. In such an embodiment, hook-and-loop portions 180 can be separated and return electrode 174 positioned around a portion of the patient's body. Hook-and-loop portions 180 can then be secured together to secure return electrode 174 around the patient. The tightness of return electrode 174 can be adjusted by changing the degree to which hook-and-loop portions 180 of return electrode 174 overlap one another.

One will appreciate that a number of other securement mechanisms known in the art may also be employed in one or more other embodiments of return electrode 174 to ensure that return electrode 174 is wearable over at least a portion of the body of a patient as described herein. Such mechanisms may include, but are not limited to, pressure adhesives, buttons, zippers, clips, laces, and the like.

In addition, the various embodiments and elements of electrosurgical systems described herein are not necessarily exclusive of one another. Rather, some or all of the features described in each embodiment and/or element of electrosurgical systems described herein may be combined together with features and/or elements of other embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. An electrosurgical return electrode, comprising:
a first pad;
a second pad; and
a conductive fabric layer disposed between the first and second pads;
an electrical bus bar electrically connected to the conductive fabric layer, the electrical bus bar comprising an insulating layer covering a surface of the bus bar that faces towards a patient's body when the electrosurgical return electrode is wrapped around a part of the patient's body and an uninsulated portion that is not covered by the insulating layer, the uninsulated portion of the bus bar and the first or second pad being configured to facilitate a capacitive connection to a capacitive connector of an electro surgical wave generator external to the first and second pads; and
one or more attachment features associated with the first pad or the second pad,
wherein the electrosurgical return electrode is devoid of any externally exposed electrical connectors in electrical contact with the conductive fabric layer,
wherein the electrosurgical return electrode is configured to be wrapped around and generally conform to a substantial portion of the part of the patient's body, and
wherein the one or more attachment features are configured to selectively secure the electrosurgical return electrode around the part of the patient's body.

2. The electrosurgical return electrode of claim 1, wherein the conductive fabric layer is transparent to radio-frequency waves, microwave radiation, infra-red (IR) radiation, ultraviolet (UV) radiation, and/or X-ray radiation.

3. The electrosurgical return electrode of claim 1, wherein the conductive fabric layer comprises:
non-conductive woven threads; and
conductive fibers embedded into the woven threads.

4. The electrosurgical return electrode of claim 1, wherein the conductive fabric layer comprises woven conductive threads.

5. The electrosurgical return electrode of claim 1, wherein the conductive fabric layer comprises conductive threads woven together with non-conductive threads.

6. The electrosurgical return electrode of claim 1, wherein the conductive fabric layer is completely surrounded by the first and second pads so that no portion of the conductive fabric layer is exposed outside of the first and second pads.

7. The electrosurgical return electrode of claim 1, wherein the conductive fabric layer is transparent to one or more wavelengths of electromagnetic radiation.

8. The electrosurgical return electrode of claim 1, wherein the electrical bus bar is flexible.

9. An electrosurgical return electrode, comprising:
a first pad;
a second pad;
a conductive element disposed between the first and second pads, the conductive element comprising:
a flexible conductive fabric that is transparent to one or more wavelengths of electromagnetic radiation; and
a bus bar disposed along an edge of the flexible conductive fabric, the bus bar having a first major surface facing the first pad and a second major surface facing the second pad, the first major surface being entirely covered by an insulating layer, and at least a portion of the second major surface of the bus bar being uncovered by the insulating layer, the uncovered portion of the second major surface of the bus bar and the second pad being configured to facilitate a capacitive connection between the bus bar and an electrical connector of an electrosurgical wave generator;
whrein the electrosurgical return electrode is devoid of any externally exposed electrical connectors in electrical contact with the flexible conductive fabric.

10. The electrosurgical return electrode of claim 9, wherein the bus bar is flexible such that the bus bar can be bent and folded without breaking during shipping or storage.

11. The electrosurgical return electrode of claim 9, wherein the bus bar comprises another flexible conductive fabric.

12. The electrosurgical return electrode of claim 9, wherein the flexible conductive fabric comprises:
 woven, non-conductive threads; and
 conductive fibers embedded in the woven, non-conductive threads.

13. The electrosurgical return electrode of claim 9, wherein the flexible conductive fabric comprises woven conductive threads.

14. The electrosurgical return electrode of claim 13, wherein the woven conductive threads are formed of silver plated nylon.

15. The electrosurgical return electrode of claim 14, wherein the woven conductive threads comprise a silver to nylon ratio of about 3:1.

16. An electrosurgical system, comprising:
 a return electrode comprising:
  a first pad;
  a second pad;
  a conductive element disposed between the first and second pad such that the first and second pads completely encompass the conductive element, the conductive element comprising:
   a flexible conductive fabric the is transparent to one or more wavelengths of electromagnetic radiation; and
   a bus bar disposed along an edge of the flexible conductive fabric, the bus bar having a first major surface facing the first pad and a second major surface facing the second pad, the first major surface being entirely covered by an insulating layer, and at least a portion of the second surface of the bus bar being uncovered by an insulating layer, the uncovered portion of the second surface of the bus bar and the second pad being configured to facilitate a capacitive connection between the bus bar and an electrical connector of an electrosurgical wave generator; and
  one or more attachment features associated with the first pad or the second pad,
  wherein the return electrode is configured to be wrapped around and generally conform to a substantial portion of a part of a patient's body and the one or more attachment features are configured to secure the return electrode around the part of the patient's body;
  wherein the return electrode is devoid of any externally exposed electrical connectors in electrical contact with the flexible conductive fabric.

17. The electrosurgical system of claim 16, further comprising the capacitive connector removably secured to the return electrode, the capacitive connector being configured to make a capacitive electrical connection with the conductive element.

\* \* \* \* \*